(12) United States Patent
Andrés et al.

(10) Patent No.: US 7,858,821 B2
(45) Date of Patent: Dec. 28, 2010

(54) INTERMEDIATE COMPOUNDS USEFUL TO PREPARE DOLASETRON

(75) Inventors: Juan Antonio Pérez Andrés, Barcelona (ES); Pere Dalmases Barjoan, Barcelona (ES); Joan Huguet Clotet, Barcelona (ES)

(73) Assignee: INKE, S.A., Barcelona (ES)

( * ) Notice: Subject to any disclaimer, the term of this patent is extended or adjusted under 35 U.S.C. 154(b) by 182 days.

(21) Appl. No.: 12/017,709

(22) Filed: Jan. 22, 2008

(65) Prior Publication Data

US 2009/0124807 A1    May 14, 2009

(30) Foreign Application Priority Data

Nov. 13, 2007    (EP)    .................................. 07380317

(51) Int. Cl.
*C07C 69/66*    (2006.01)

(52) U.S. Cl. ..................................................... 560/186
(58) Field of Classification Search ................. 560/189, 560/186
See application file for complete search history.

(56) References Cited

FOREIGN PATENT DOCUMENTS

| EP | 266730 | 5/1988 |
|----|--------|--------|
| EP | 339669 | 11/1989 |
| WO | WO2006056081 | 6/2006 |
| WO | WO2007003522 | 11/2007 |

*Primary Examiner*—Taylor Victor Oh
(74) *Attorney, Agent, or Firm*—Tristan A. Fuierer; Moore & Van Allen PLLC

(57) ABSTRACT

The present invention relates to intermediates useful in the synthesis of Dolasetron and synthetic precursors thereof, as well as to processes for obtaining them. In addition, it refers to the hydrochloric salt of Dolasetron and polymorphic forms of Dolasetron and precursors thereof.

12 Claims, 5 Drawing Sheets

INTERMEDIATE COMPOUNDS USEFUL TO PREPARE DOLASETRON

CROSS REFERENCE TO RELATED APPLICATIONS

This application claims priority to European Patent Application No. EP07380317.3, filed Nov. 13, 2007 and entitled "Intermediate Compounds Useful to Prepare Dolasetron" in the name of Juan Antonio Pérez Andrés, Pere Dalmases Barjoan and Joan Huguet Clotet, incorporated herein by reference.

FIELD OF THE INVENTION

The present invention relates to intermediates useful in the synthesis of the compound Dolasetron, as well as to processes for obtaining them. In addition, it relates to polymorphic forms of precursors thereof.

BACKGROUND

Dolasetron, the generic name of the compound 1H-indole-3-carboxylic acid 10-oxo-8-aza-tricyclo[$5.3.1.0^{3,8}$]undec-5-yl ester, is a pharmaceutically active compound widely known for its anti-emetic and anti-nausea properties. Its molecular formula responds to the following structure:

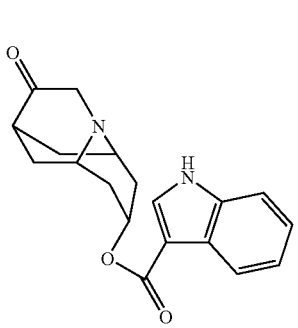

I

Dolasetron was described for the first time in patent EP 0266730. Said patent describes the preparation of Dolasetron and analogues compounds by a process which includes, as its last step, the esterification of 5-hydroxy-8-azatricyclo[$5.3.1.0^{3,8}$]-undecan-10-one (compound II) and the indole-3-carboxylic acid (compound III):

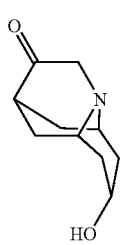

II

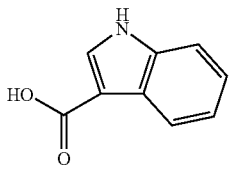

III

European patent application EP0339669 also describes the preparation of Dolasetron using, as the last step, the esterification reaction between compound II and the anhydride formed from the compound III and the trifluoroacetic acid.

In EP0266730 it is described the preparation of the alcohol II (scheme 1) starting from an alkyl cyclopenten-1-carboxylate, which is oxidized to a 1,2-diol using N-methyl morpholine N-oxide, and $OsO_4$ as catalyst. This diol is then cleaved to the corresponding dialdehyde using sodium metaperiodate. A Robinson-Schöpf cyclisation of the dialdehyde with a lower alkyl glycine ester and acetonedicarboxylic acid yields the formation of a ketone. This ketone is reduced to an alcohol using sodium borohydride and the product is reacted with dihydropyran to protect the hydroxyl group. Dieckmann cyclisation using a strong base and dealkoxycarbonylation yields the desired alcohol II.

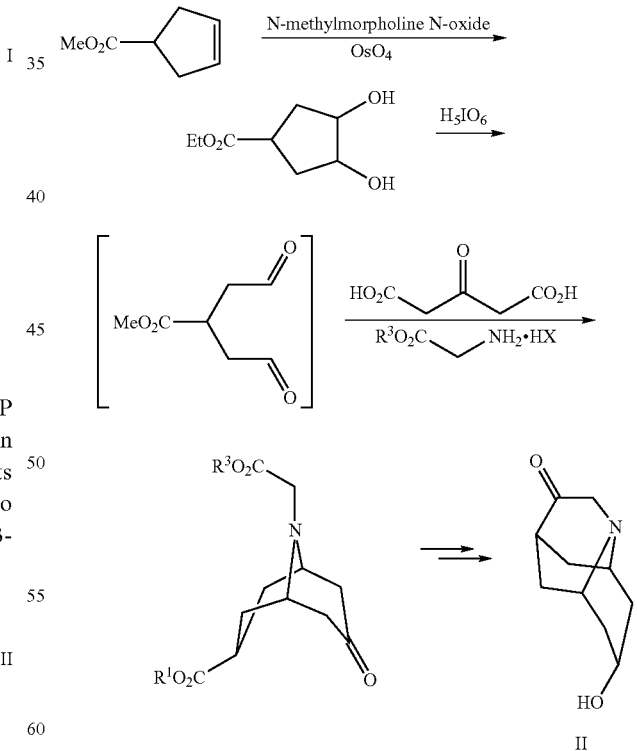

Scheme 1

EP0339669 also describes the oxidation of the cyclopenten-1-carboxylates using ozone (Scheme 2) or m-chloroperbenzoic (Scheme 3) acid and periodic acid to obtain the corresponding dialdehyde.

Scheme 2

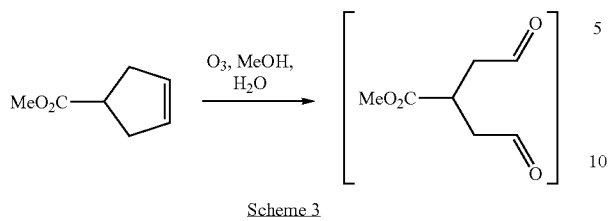

Scheme 3

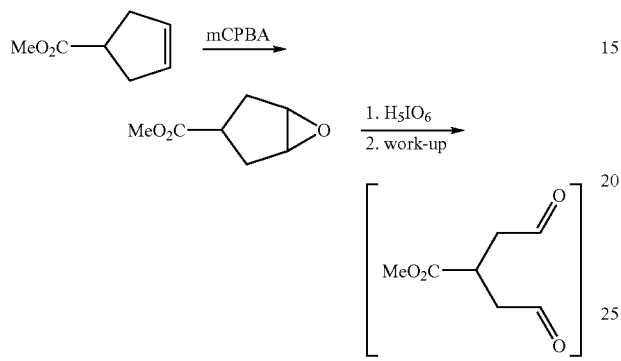

Scheme 4

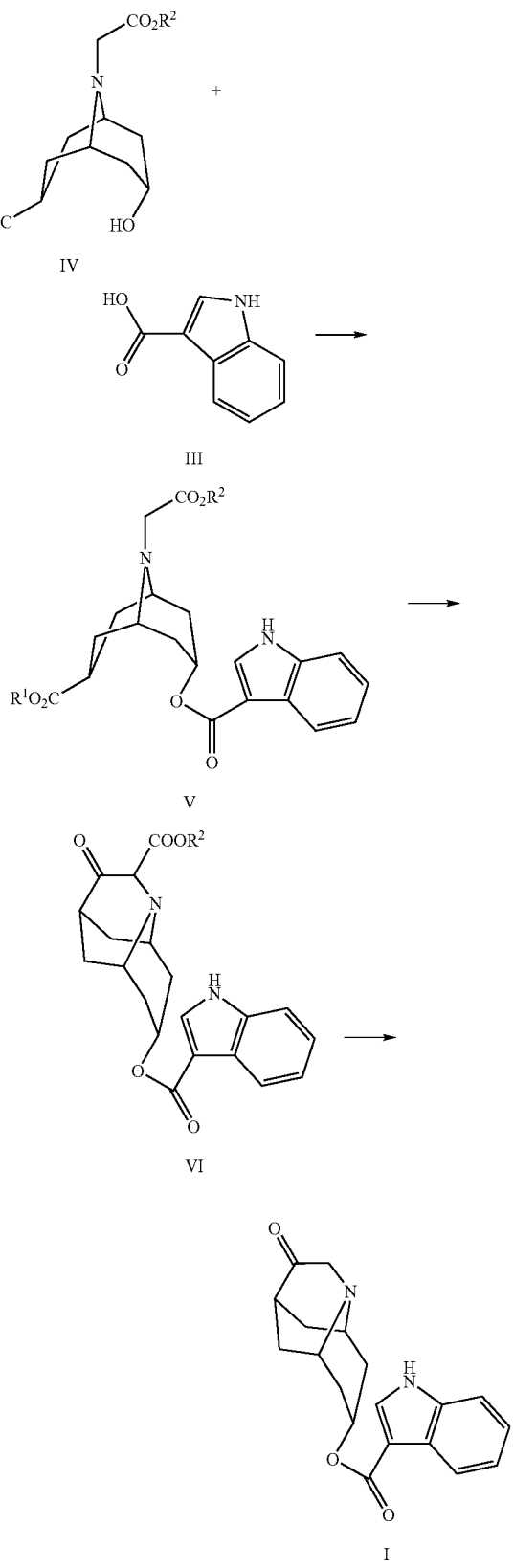

Nevertheless, the processes described in said patents present some disadvantages since they show many synthetic steps, using dangerous and toxic reactants, and complex work-up. For example, the synthesis of compound II requires the use of precursors with protecting groups, thus lengthening the synthetic route and entailing a reduction of atomic efficiency. Moreover, the selected protecting group (tetrahydropyranyl) leads to a mixture of diastereoisomers instead of to a single pure product. In addition, the handling and purification of said precursor has proved to be very complex at industrial scale since said mixture has an oily consistency.

Another notable drawback is that column chromatography is used to carry out the purification of the mixture of diastereoisomers, not being possible to use other methods such as crystallization or distillation. This disadvantage, together with the reduction in the atomic efficiency remarked upon above, entails a considerable increase of residues, thus leading to environmental problems.

Furthermore, the preparation of compound II includes a process of extraction of the product from an aqueous phase with ethyl acetate which requires both, numerous steps due to the high solubility of said compound in water, and specific installations.

International application WO2007/003522 solves some of the drawbacks mentioned above, thus providing a process for the preparation of Dolasetron characterized by the fact that there is no need to use protecting groups, also showing fewer steps. The process described therein consists of an esterification reaction of an alcohol IV with indole-3-carboxylic acid; a Dieckmann reaction of the intermediate formed by reaction with a strong organic or inorganic base; and the subsequent dealcoxycarbonylation (Scheme 4).

However, there is a need in the art to provide alternative or improved methods to obtain Dolasetron by the development of new intermediates which avoid, or at least reduce, the problems described above.

On the other hand, there are documents in the state of the art which disclose some of the reactants or intermediates used in the present invention. For example, in Herrmann, J. L. et al. "Ketene thioacetal monoxides. Novel and versatile class of two-carbon Michael Receptors", *Tetrahedron Lett.* 1973, 47, 4711-4714, and in Strukov, I. T. "Thiazolidinecarboxylic acid and its derivatives. I. The compound with thiazolidine-pyrrolidine ring system", *Zhurnal Obshchei Khimii*. 1952, 22, 521-527, there are disclosed mono-alkylated malonates such as those used in the present invention, namely as compound of formula XIII.

In WO2006/056081 it is described the mesylate of the tricyclic ketone ($R^1$ and $R^3$=Ethyl) of the compound of formula IX of the present invention, this is the only salt described of a compound of such general formula.

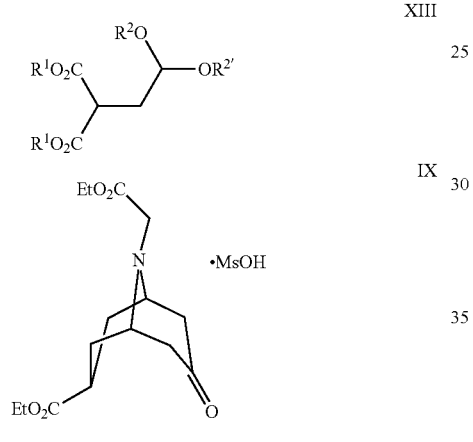

XIII

IX

BRIEF DESCRIPTION OF THE INVENTION

The authors of the present invention have found that the compound of formula (VII) is a very suitable intermediate in the synthetic route of the compound Dolasetron since it allows preparing precursors thereof with good yields and fewer steps.

The use of this compound VII in the synthesis of precursors of Dolasetron overcomes many of the disadvantages of the prior art, since it is not necessary to use dangerous and toxic reactants and there is no need to use specific instrumentation.

Therefore, in a first aspect, the present invention relates to a compound of formula (VII):

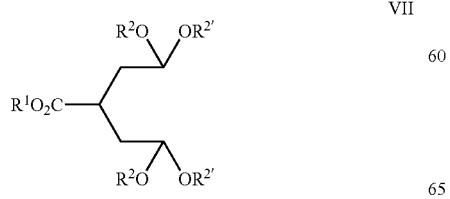

VII wherein
$R^1$ is $C_1$-$C_6$ branched or linear alkyl, and
$R^2$ and $R^{2'}$ are independently a $C_1$-$C_6$ branched or linear alkyl, or both $R^2$ and $R^{2'}$ attached respectively to the oxygen atoms belonging to the same carbon atom form a cycle.

A second aspect of the invention refers to a process for preparing a compound of formula (VII), comprising the dealkoxycarbonylation of a compound of formula (VIII) in the presence of a salt and a solvent:

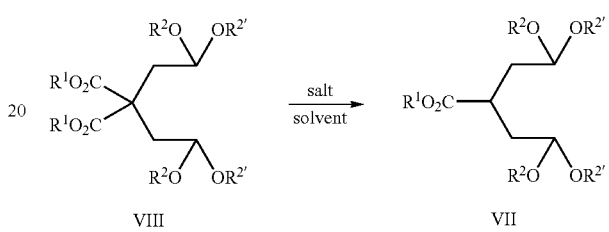

VIII        VII wherein $R^1$, $R^2$ and $R^{2'}$ are as previously defined.

Another aspect relates to a compound of formula (VIII):

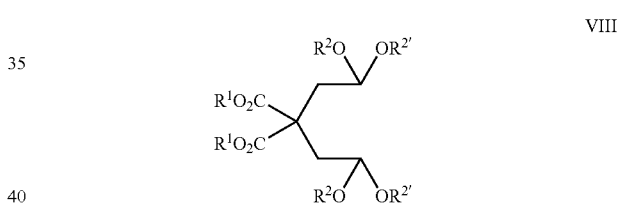

VIII wherein $R^1$, $R^2$ and $R^{2'}$ are as defined above.

In another aspect the present invention refers to the use of a compound of formula (VII) in the preparation of a compound of formula (IX):

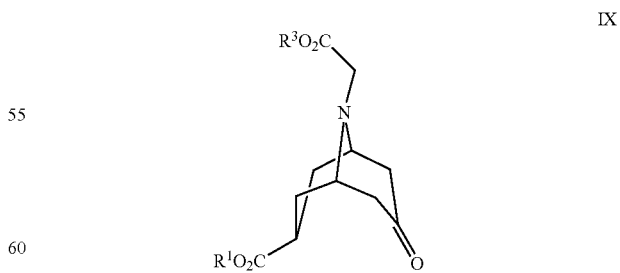

IX wherein $R^1$ is a $C_1$-$C_6$ branched or linear alkyl and $R^3$ is methyl or ethyl.

It also refers to the use of a compound of formula (VII) in the preparation of Dolasetron (I):

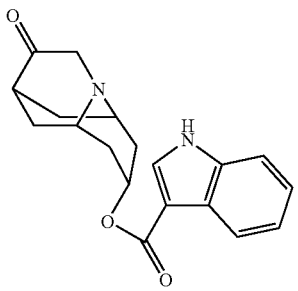

I

Another aspect of the invention is a process for the preparation of a compound of formula (IX) or a salt thereof which comprises:
  i. hydrolyzing the compound of formula (VII) to yield a compound of formula (X):

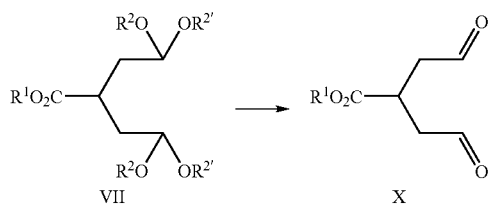

ii. converting compound of formula (X) into the compound of formula (IX); and optionally,
  iii. converting compound of formula (IX) into a salt thereof;
  wherein $R^1$, $R^2$ and $R^{2'}$ are as previously defined.

The skilled in the art is aware that a compound X in an aqueous medium can be in hydratated form forming related substances that are also the object of the present invention.

In another aspect, the invention relates to a process for preparing Dolasetron (I) which comprises the process as defined just above and, subsequently, the conversion of the compound of formula (IX) into Dolasetron (I).

Another aspect refers to the hydrochloride salt of the compound of formula (IX·HCl).

Another aspect refers to the polymorph form I of the monohydrate of the hydrochloride salt of the compound of formula (IX·HCl·H$_2$O) characterized by the XRPD showed in FIG. 1 and the following peaks XRPD (2θ): 8.5, 10.3, 11.3, 14.5, 15.1, 16.8, 19.4, 20.7, 21.0, 21.4, 21.7, 22.4, 23.8, 24.5, 25.3, 25.7, 26.0, 26.2, 26.4, 28.3, 29.5, 30.1, 30.5, 32.0, 32.5, 36.5, 37.0.

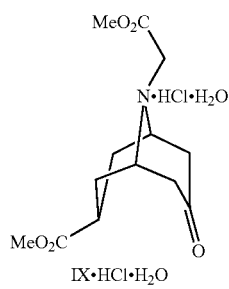

IX·HCl·H$_2$O

Finally, the present invention relates to the hydrochloride salt of the compound of formula (V):

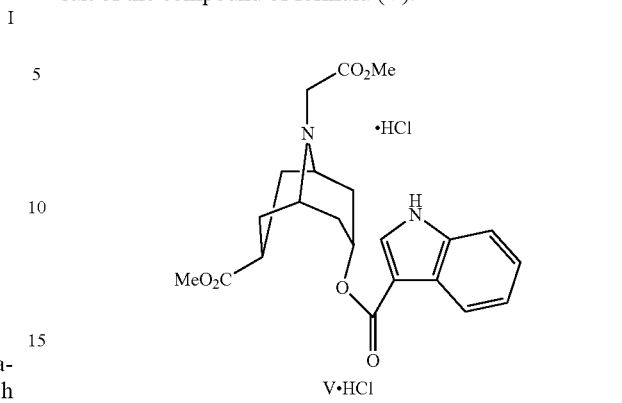

V·HCl

It also relates to the polymorph form I of the hydrochloride salt of the compound of formula (V·HCl) characterized by the XRPD showed in FIG. 3 and the following peaks XRPD (2θ): 8.1, 9.2, 12.4, 13.1, 14.5, 14.7, 15.7, 16.2, 16.5, 16.8, 17.4, 18.5, 18.7, 19.0, 19.5, 20.6, 21.0, 21.9, 22.7, 23.0, 23.3, 23.5, 23.9, 25.2.

DETAILED DESCRIPTION OF THE INVENTION

Figure 1:
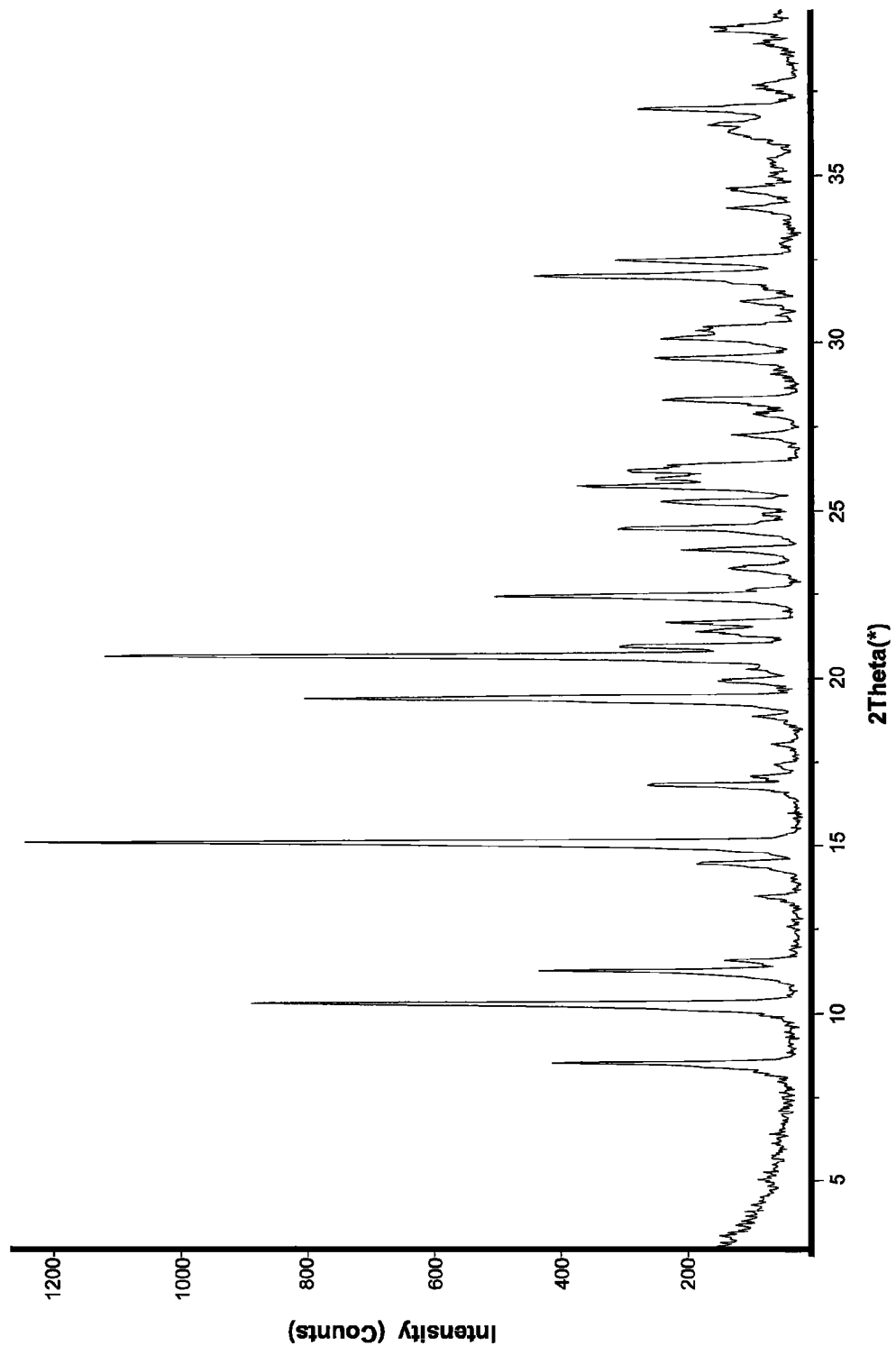
FIG. 1: XRPD of polymorph form I of 9-methoxycarbonylmethyl-7-oxo-9-aza-bicyclo[3.3.1]nonane-3-carboxylic acid methyl ester hydrochloride monohydrate (IX·HCl·H$_2$O).
Figure 2:
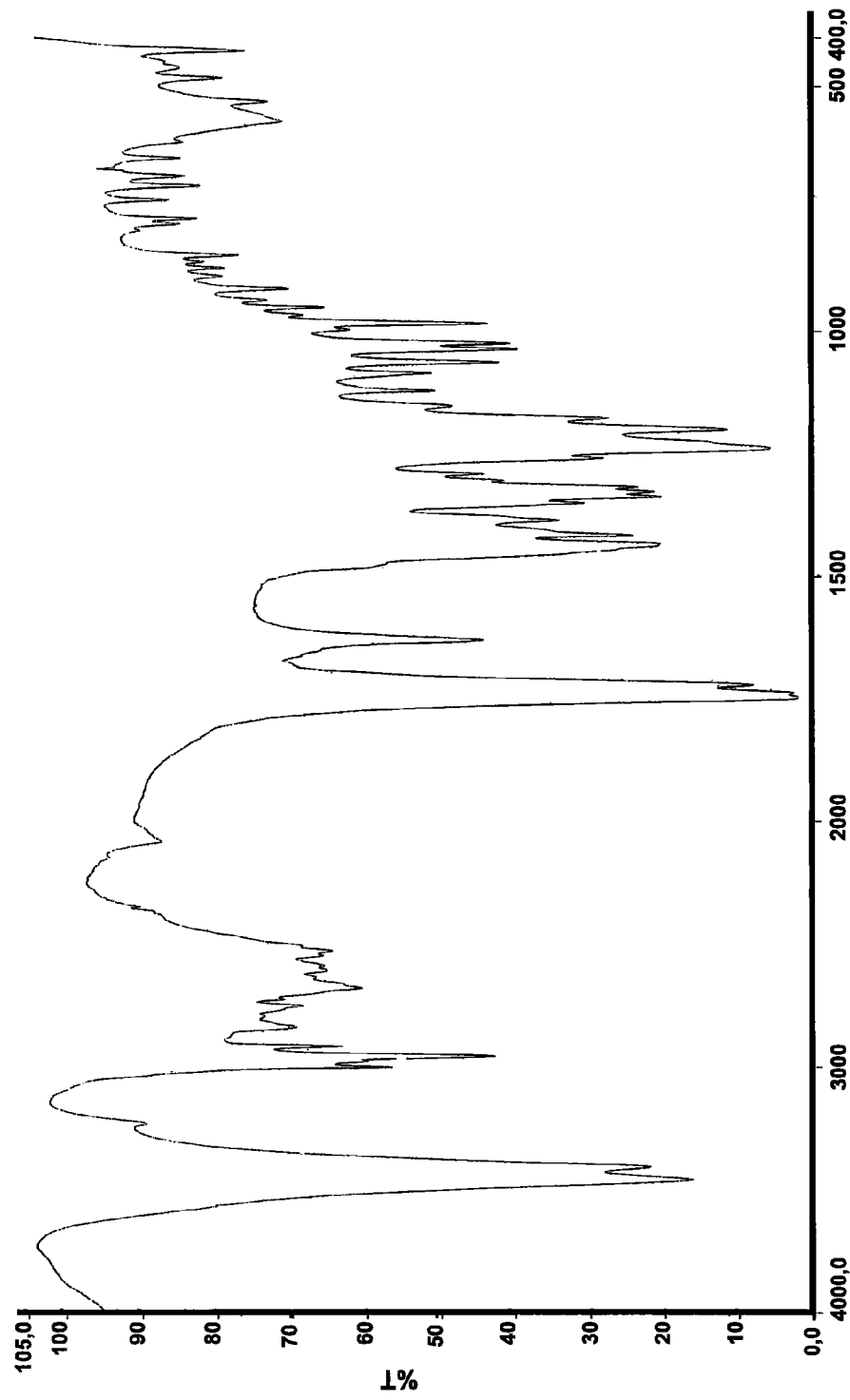
FIG. 2: IR of polymorph form I of 9-methoxycarbonylmethyl-7-oxo-9-aza-bicyclo[3.3.1]nonane-3-carboxylic acid methyl ester hydrochloride monohydrate (IX·HCl·H$_2$O).

In the context of the present invention, the following terms have the meaning detailed below:

The term "Dolasetron" in the present application refers to the base form. Even that, it is known to the skilled in the art that when the base is available, it can be converted into an acid addition salt thereof by known methods.

The term "linear or branched $C_1$-$C_6$ alkyl" relates to a linear or branched hydrocarbon radical consisting of carbon and hydrogen atoms, which does not contain unsaturation, having one to six carbon atoms and which is joined to the rest of the molecule by a single bond. Examples of alkyl groups include methyl, ethyl, propyl, isopropyl, butyl, isobutyl, tertbutyl, sec-butyl, pentyl and hexyl.

By the term "substituted or unsubstituted alkyl" it is understood a linear hydrocarbon radical consisting of carbon and hydrogen atoms, which does not contain unsaturation, having one to twelve carbon atoms and which is joint to the rest of the molecule by a single bond. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc.

The term "substituted or unsubstituted aryl" relates to an aromatic hydrocarbon radical containing from 1 to 3 separated or fused rings and from 6 to about 18 carbon ring atoms, such as phenyl, naphthyl, indenyl, phenanthryl or anthracyl radical. The aryl radical may be optionally substituted by one or more substituents such as hydroxy, mercapto, halo, alkyl, phenyl, alkoxy, haloalkyl, nitro, cyano, dialkylamino, aminoalkyl, acyl, alkoxycarbonyl, etc.

By the term "fluorinated hydrocarbon" it is understood a linear hydrocarbonated radical which is substituted by one or more fluorine atoms. Examples or fluorinated hydrocarbons are trifluoromethyl, trifluoroethyl, etc...

The term "polar aprotic solvent" relates to a polar solvent that is not capable of exchanging protons with the reagents and that has no polarizable proton. Examples of polar aprotic solvents are dimethylformamide, N-methylpyrrolidone and dimethylacetamide. Preferably the polar aprotic solvent is dimethylformamide.

The term "step-wise reaction" means two or more reactions that take place isolating the intermediate compounds.

The term "one-pot reaction" means two or more reactions that take place without isolating intermediate compounds, wherein all the reactants are added at the beginning of the first reaction or sequentially during the course of the reaction.

The term "leaving group" refers to a group that can easily be replaced by another group. In J. March Advanced Organic Chemistry, 4$^{th}$ edition, 1992, are listed some typical leaving groups. In the context of the present invention, the leaving groups are preferably selected from halogens and activated alcohols, such as sulphonyloxy groups. The halogens include fluorine, chlorine, bromine and iodine. The sulphonyloxy group is represented by —OSO$_2$R, wherein R is a substituted or unsubstituted alkyl, a substituted or unsubstituted aryl, a fluorinated hydrocarbon or a halogen. Preferably R is methyl, p-toluoyl, trifluoromethyl or fluorine.

The Krapcho dealkoxycarbonylation reaction in the present invention is defined as described in the Merck Index Thirteen Edition, Organic Name Reaction section, page ONR-60, reaction 225. It is the reaction of a malonate diester that reacts with a salt in a polar aprotic solvent to yield an ester.

The Robinson-Schöpf condensation in the present invention is defined as described in the Merck Index Thirteen Edition, Organic Name Reactions section, page ONR-90, reaction 343. It is a reaction to prepare tropinones from a dialdehyde, methylamine and acetonedicarboxylic acid.

In a first aspect the present invention relates to a compound of formula (VII):

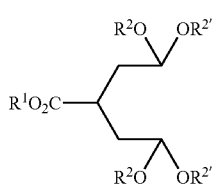

VII wherein
R$^1$ is C$_1$-C$_6$ branched or linear alkyl, and
R$^2$ and R$^{2'}$ are independently a C$_1$-C$_6$ branched or linear alkyl, or both R$^2$ and R$^{2'}$ attached respectively to the oxygen atoms belonging to the same carbon atom form a cycle.

In a particular embodiment, radicals R$^1$, R$^2$ and R$^{2'}$ are independently methyl or ethyl. In a preferably embodiment, R$^1$, R$^2$ and R$^{2'}$ are methyl. Even in another preferred embodiment R$^1$, R$^2$ and R$^{2'}$ are ethyl.

The use of different R$^1$, R$^2$ and R$^{2'}$ results in the same final compound, but the intermediates are less pure due to trans-esterifications. These trans-esterificated compounds yield also to the same final product.

In another particular embodiment, both R$^2$ and R$^{2'}$, attached respectively to the oxygen atoms belonging to the same carbon atom, form a cycle.

The process for the preparation of the compound of formula (VII) comprises the dealkoxycarbonylation of a compound of formula (VIII). Said process is carried out in the presence of a salt and a solvent.

In a particular embodiment, the salt used in the process of dealkoxycarbonylation is a halide of an alkali metal, preferably selected from LiCl, NaCl, LiBr, NaBr, KBr and NaI, more preferably NaBr.

In another particular embodiment, the solvent is a polar aprotic solvent, preferably selected form dimethylformamide, N-methylpyrrolidone and dimethylacetamide, more preferably dimethylformamide.

The reaction of dealkoxycarbonylation can also take place in the presence of water, being possible to add up to 2 equivalents with respect to the compound of formula (XII). However, it is preferred to carry out said reaction in the absence of water.

In another particular embodiment, the reaction temperature may ranges between 80° C. and the boiling point of the solvent, preferably between 120 and 150° C., more preferably between 140 and 150° C.

The process for the preparation of the compound (VII) of the invention may further comprise previous dialkylation of a malonate of formula (XI) with a compound of formula (XII) in the presence of a base and a solvent to obtain the compound of formula (VIII), according to the following synthesis scheme:

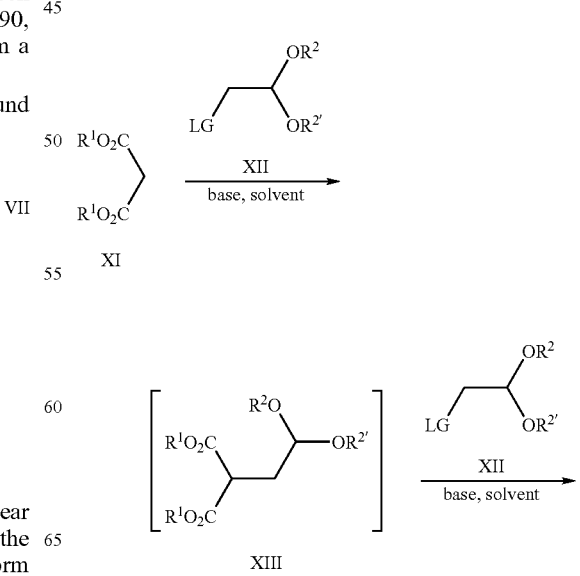

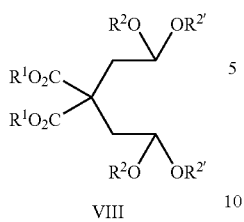

VIII

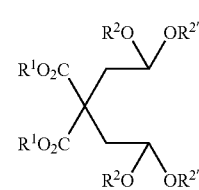

VIII wherein $R^1$, $R^2$ and $R^{2'}$ are as defined previously and LG is a leaving group as previously defined.

The dialkylation may be carried out in a one-pot reaction or in a step-wise reaction.

When performed as a one-pot reaction the first and second alkylation take place without isolating the intermediate compound of formula (XIII), adding all reactants at the beginning of the first reaction or sequentially during the course of the reaction.

However, said process can also be achieved as a step-wise reaction, i.e., a first alkylation reaction is carried out, thus isolating compound of formula (XIII) and subsequently, second alkylation takes place in the same conditions as the first alkylation.

After dialkylation reaction has concluded, it is possible to isolate compound of formula (VIII) in order to be used for the preparation of compound of formula (VII). Alternatively, the dealkoxycarbonylation reaction can be achieved subsequently in the same reaction without isolating compound (VIII).

The temperature for the alkylation reactions can range from 50° C. to the boiling point of the solvent, preferably from 70 to 120° C., preferably 90° C. for the monoalkylation, whereas preferably 120° C. for the dialkylation.

In a particular embodiment of the invention, the alkylating agent of formula (XII) can be selected from the group consisting of 2-bromo-1,1-dimethoxy-ethane, 2-bromo-1,1-diethoxy-ethane and 2-bromomethyl-[1,3]dioxolane, more preferably 2-bromo-1,1-dimethoxy-ethane or 2-bromo-1,1-diethoxy-ethane, even more preferably 2-bromo-1,1-dimethoxy-ethane. Said alkylating agent is added to the reaction in a quantity that ranges form 1 to 1.4 equivalents, preferably 1 equivalent with respect to the malonate of formula (XI).

In another particular embodiment, the base used in the dialkylation reaction is selected from metallic hydrides, such as LiH, NaH, KH or $CaH_2$, and metallic alcoholates, such as t-BuOK, EtONa, MeONa or MeOK, being preferably the use of metallic alcoholates, more particularly MeOK.

Regarding the solvent, it can be used polar aprotic solvents such as dimethylformamide, N-methylpyrrolidine or dimethylacetamide, more preferably dimethylformamide.

Compounds of formula (XI) and (XII) are commercially available or can be synthesized by any method known by a skilled person.

The compound of formula (VIII) used to prepare compound of formula (VII) constitutes also another aspect of the present invention:

wherein $R^1$, $R^2$ and $R^{2'}$ are as previously defined for compound of formula (VII).

In a particular embodiment, $R^1$, $R^2$ and $R^{2'}$ are methyl. In another particular embodiment, $R^1$, $R^2$ and $R^{2'}$ are ethyl. Even in another particular embodiment, $R^2$ and $R^{2'}$ attached respectively to the oxygen atoms belonging to the same carbon atom form a cycle.

Another aspect of the present invention refers to the use of the compound of formula (VII) for the preparation of a compound of formula (IX) or a salt thereof:

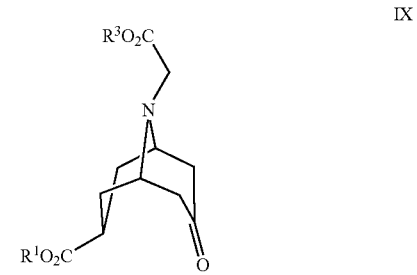

IX wherein $R^1$ is a $C_1$-$C_6$ branched or linear alkyl and $R^3$ is methyl or ethyl.

Said compound (IX) is a precursor in the synthesis of the compound Dolasetron as described in patent application WO2007/003522, which is herein incorporated by reference.

The process for preparing a compound of formula (IX) from compound of formula (VII) is also another aspect of the present invention. Thus, said process comprises:

i) hydrolyzing the compound of formula (VII) to yield a compound of formula (X):

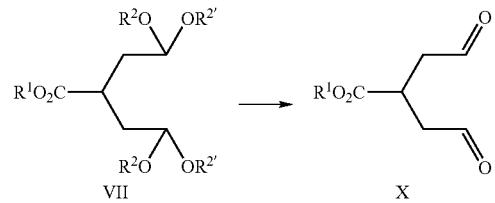

ii) converting compound of formula (X) into the compound of formula (IX); and optionally,
iii) converting compound of formula (IX) into a salt thereof,
wherein $R^1$, $R^2$ and $R^{2'}$ are as previously defined.

The hydrolysis reaction can take place in the presence of an acid, such as hydrochloride, and water, in a quantity which ranges from 1 to 20 volumes of HCl 1M, preferably 7 to 13 volumes, even more preferably 10 volumes. The temperature may vary from 0 to 40° C., although it is preferred to carry out the reaction at about 20° C. The reaction time ranges from 1 to 6 hours, preferably 1 hour. Compound of formula (X) can be isolated or, alternatively, the step ii) can be carried out in the same reaction medium.

The conversion of the compound of formula (X) into the compound of formula (IX) can be carried out by any method known in the state of the art, such as those described in EP0339669. Said process can course by a Robinson-Schöpf condensation, which comprises the reaction between the compound of formula (X) and the compounds of formula (XIV) and (XV), optionally in the presence of a base:

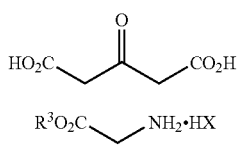

XIV

XV wherein $R^3$ is methyl or ethyl and HX is an acid.

Said reaction preferably takes place at a pH between 1 and 3.

The base, optionally used in the condensation reaction, can be selected from phosphates, acetates such as: $Na_2HPO_4$, $NaH_2PO_4$, AcONa, $K_2HPO_4$, $KH_2PO_4$ and potassium hydrogenphtalate.

In a particular embodiment, the process continues with the conversion of compound of formula (IX) into one of its salts. In a particular embodiment, the salt to be obtained is the hydrochloride salt. Said salt can be prepared by reacting a solution of the compound of formula (IX) with a source of HCl, for example an anhydrous source of HCl, such as HCl gas or chlorotrimethylsilane, or an aqueous source of HCl, such as concentrated HCl.

In another aspect, the present invention relates to a process for preparing a compound of formula (IX) or a salt thereof, which comprises all the steps mentioned in the processes described above, using the compound of formula (XI) as starting compound. Therefore, said process comprises:

a) dialkylation of the malonate of formula (XI) with a compound of formula (XII) in the presence of a base and a solvent to obtain the compound of formula (VIII):

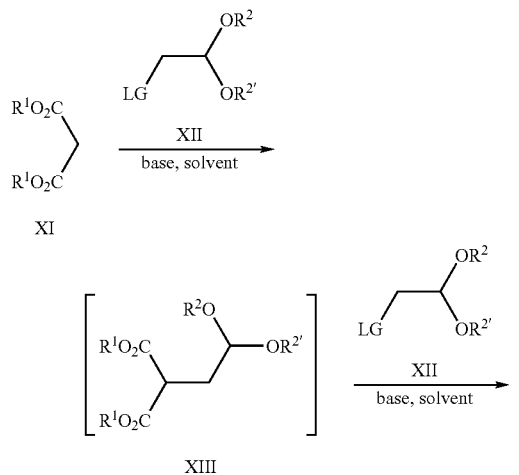

-continued

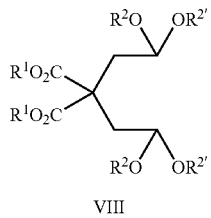

VIII b) dealkoxycarbonylation of a compound of formula (VIII) in the presence of a salt and a solvent to obtain a compound of formula (VII):

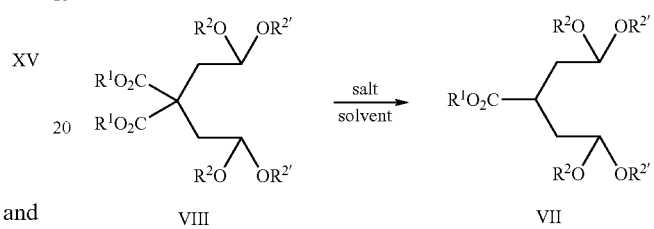

c) hydrolyzing the compound of formula (VII) to yield a compound of formula (X):

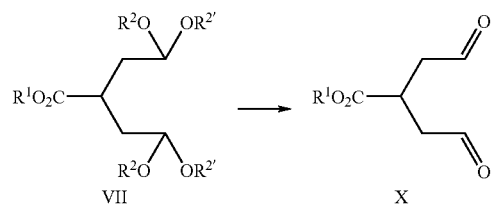

d) converting compound of formula (X) into the compound of formula (IX); and optionally, e) converting compound of formula (IX) into a salt thereof, wherein $R^1$, $R^2$ and $R^{2'}$ are as defined previously.

Steps a) and b) can be performed as a one-pot or step-wise reaction. Steps c), d) and e) can be performed as a one-pot or step-wise reaction. However, alternatively, intermediates VII, VIII, XIII, X and/or IX can be isolated after finishing the corresponding step.

The skilled in the art is aware that a compound X in an aqueous medium can be in hydratated form forming related substances that are also the object of the present invention.

In another aspect, the present invention relates to the use of the compound of formula (VII) for the preparation of the compound of formula (I), also known as Dolasetron, or a salt thereof:

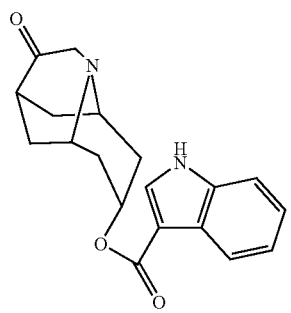

I

The process for preparing Dolasetron (I) comprises the different processes as defined above for the preparation of the compound of formula (IX) and, subsequently, the conversion of the compound of formula (IX) or a salt thereof into Dolasetron (I) and, optionally, the conversion of Dolasetron (I) into a salt thereof.

The conversion of compound (IX) into Dolasetron (I) can be carried out by any known method in the art. For example, the compound of formula (IX) is firstly reduced in order to transform the ketone group into a hydroxyl group in the presence of a reducing agent, such as sodium borohydride, as described in EP0339669. Subsequently, as disclosed in patent application WO2007/003522 (described in Scheme 4), said alcohol can be subjected to an esterification reaction with indole-3-carboxylic acid or a reactive derivative thereof, followed by a Dieckmann reaction with a strong organic or inorganic base and finally, a dealkoxycarbonylation provides the Dolasetron (I). Dolasetron base can be purified as described in example 8 in E0339669. If required, a pharmaceutically acceptable salt, or hydrates or solvates of Dolasetron (I) can be obtained.

It has been surprisingly found that the use of the hydrochloride salt of compound of formula (IX·HCl) in the synthesis of Dolasetron allows obtaining said compound with a high purity at the end of the process. This is due to the fact that the hydrochloride salt can be better and more easily purified than the base compound of formula (IX). Said base is obtained as a difficult to handle oily product.

Therefore, it is another aspect of the invention to provide the hydrochloride salt of the compound of formula (IX·HCl).

Therefore, it is another aspect of the invention to provide a polymorphic form I of the hydrochloride monohydrate salt of the compound of formula (IX·HCl·H$_2$O). Said polymorph is characterized by the XRPD showed in FIG. 1 and the peaks as defined in the brief description of the invention as well as by the following IR data: 3460, 3409, 3000, 2956, 1746, 1721, 1630, 1433, 1416, 1384, 1136, 1326, 1317, 1236, 1199, 1176, 1062, 1036, 1024 cm$^{-1}$. Said polymorph also has a DSC minimum at 172-174° C.

Finally, another aspect of the invention relates to a polymorphic form I of the hydrochloride salt of the compound of formula (V) which is characterized by the XRPD showed in FIG. 1 and the peaks as defined in the brief description of the invention and by the following IR data: 3148, 3103, 3082, 3060, 3026, 2924, 2850, 2510, 1743, 1727, 1700, 1601, 1493, 1452, 1175, 1028, 756, 702, 540 cm$^{-1}$. Said polymorph of the hydrochloride salt of the compound of formula (V) is further characterized by having DSC minimum at 240-242° C.

The following non-limiting examples will further illustrate specific embodiments of the invention. They are, however, not intended to be limiting the scope of the present invention in any way.

EXAMPLES

Example 1

Synthesis of 2-(2,2-Dimethoxy-ethyl)-4,4-dimethoxy-butyric acid methyl ester

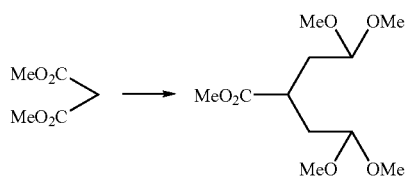

5.73 g (81.69 mmol) of MeOK are placed in a 0.5 L reactor with 100 mL DMF. 10.0 g (75.69 mmol) of dimethyl malonate are added slowly to the previous mixture keeping the temperature around 25° C. Once the addition has finished the temperature is raised to 60° C. and 8.90 mL (75.30 mmol) of bromoacetaldehyde dimethyl acetal are added. The temperature is raised to 90° C. and kept during 8 h.

The temperature is lowered to 20° C. and 5.47 g (78.0 mmol) of MeOK are added portionwise to the mixture. Once the addition has finished the temperature is raised to 60° C. and 8.90 mL (75.30 mmol) of bromoacetaldehyde dimethyl acetal are added. The temperature is raised to 120° C. and kept during 10 h.

The temperature is lowered to 20° C. and 15.58 g (151.41 mmol) of NaBr are added. The mixture is heated to 150° C., distilling methanol to reach the process temperature. The temperature is kept for 4 h.

Then, the mixture is cooled to 50° C. and the solvent is removed in vacuo. Toluene is added to the mixture, and water is slowly added. The product is extracted into the organic layer, and then a second extraction with toluene is done. The organic layers are washed with water. The toluene is distilled off, and 14.2 g (75%) of 2-(2,2-Dimethoxy-ethyl)-4,4-dimethoxy-butyric acid methyl ester are obtained as a yellowish oil.

NMR $^1$H(CDCl$_3$, 200 MHz) δ (ppm): 4.38 (t, J=5.64, 2H, C$\underline{H}$(OMe)$_2$), 3.70 (s, 3H, CO$_2$C$\underline{H}_3$), 3.31 (s, 12H, CH(OCH$_3$)$_2$), 2.70-2.56 (m, 1H, C$\underline{H}$—CO$_2$Me), 2.07-1.93 (m, 2H, C$\underline{H}_2$—CH(OMe)$_2$), 1.80-1.68 (m, 2H, C$\underline{H}_2$—CH(OMe)$_2$).

NMR $^{13}$C (CDCl$_3$, 50 MHz) δ (ppm): 175.9 (C, $\underline{C}$O$_2$Me), 103.0 (CH, $\underline{C}$H(OMe)$_2$), 53.4 and 53.1 (CH$_3$, CH(O$\underline{C}$H$_3$), 51.8 (CH$_3$, CO$_2$$\underline{C}$H$_3$), 37.7 (CH, $\underline{C}$H—CO$_2$Me), 35.5 (CH$_2$, $\underline{C}$H$_2$—CH(CO$_2$Me)$_2$).

IR (film, cm$^{-1}$): 2949, 2832, 1734, 1438, 1192, 1170, 1122, 1052.

The intermediate products of this synthesis can be isolated and characterized as yellowish oils:

2-(2,2-dimethoxy-ethyl)-malonic acid dimethyl ester

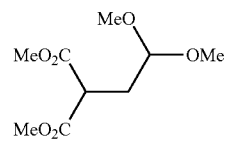

NMR $^1$H(CDCl$_3$, 200 MHz) δ (ppm): 4.42 (t, J=5.64, 1H, C$\underline{H}$(OCH$_3$)$_2$), 3.75 (s, 6H, CO$_2$C$\underline{H}_3$), 3.54 (t, J=7.25, 1H, C$\underline{H}$(CO$_2$Me)$_2$), 3.32 (s, 6H, CH(OC$\underline{H}_3$)$_2$), 2.23 (dd, J=7.25, 5.64, 2H, C$\underline{H}_2$—CH(OCH$_3$)$_2$).

NMR $^{13}$C (CDCl$_3$, 50 MHz) δ (ppm): 170.9 (C, $\underline{C}$O$_2$CH$_3$), 103.8 (CH, $\underline{C}$H(OCH$_3$)$_2$), 54.9 (CH$_3$, CO$_2$$\underline{C}$H$_3$), 53.7 (CH$_3$, CH(O$\underline{C}$H$_3$)$_2$), 48.8 (CH, $\underline{C}$H(CO$_2$CH$_3$)$_2$), 33.2 (CH$_2$, $\underline{C}$H$_2$—CH(OCH$_3$)$_2$).

IR (film, cm$^{-1}$): 2955, 2835, 1733, 1436, 1124, 1059.

2,2-Bis-(2,2-dimethoxy-ethyl)-malonic acid dimethyl ester

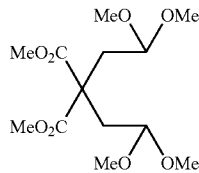

NMR $^1$H (CDCl$_3$, 200 MHz) δ (ppm): 4.42 (t, J=5.64, 2H, C$\underline{H}$(OCH$_3$)$_2$), 3.70 (s, 6H, CO$_2$C$\underline{H}_3$), 3.31 (s, 12H, CH(OC$\underline{H}_3$)$_2$), 2.29 (d, J=5.64, 4H, C$\underline{H}_2$—CH(OCH$_3$)$_2$).

NMR $^{13}$C (CDCl$_3$, 50 MHz) δ (ppm): 171.4 (C, $\underline{C}$O$_2$CH$_3$), 102.1 (CH, $\underline{C}$H(OCH$_3$)$_2$), 53.8 (CH$_3$, CO$_2\underline{C}$H$_3$), 52.9 (C, $\underline{C}$(CO$_2$CH$_3$)$_2$), 52.5 (CH$_3$, CH(O$\underline{C}$H$_3$)$_2$), 36.2 ($\underline{C}$H$_2$, CH$_2$—CH(OMe)$_2$).

IR (film, cm$^{-1}$): 2953, 2834, 1733, 1436, 1181, 1115, 1048.

Example 2

Synthesis of 2-(2,2-diethoxy-ethyl)-malonic acid dimethyl ester

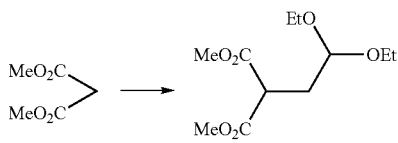

9.1 g (81 mmol) of $^t$BuOK are placed in a 250 mL reactor with 100 mL of DMF. 10.0 g (75.7 mmol) of dimethyl malonate are added slowly to the previous mixture keeping the temperature around 25° C. Once the addition has finished the temperature is raised to 60° C. and 14.9 g (75.7 mmol) of bromoacetaldehyde diethyl acetal are added. The temperature is raised to 90° C. and kept during 8 h.

The temperature is lowered to 20° C. and the solvent evaporated in vacuo. Toluene is added to the mixture, and water is slowly added. The product is extracted into the organic layer, then a second extraction with water is done and the toluene is distilled. 14.1 g (75%) of 2-(2,2-diethoxy-ethyl)-malonic acid dimethyl ester are obtained as a colorless oil.

NMR $^1$H (CDCl$_3$, 200 MHz) δ (ppm): 4.52 (t, 1H, C$\underline{H}$(OEt)$_2$), 3.78 (s, 6H, CO$_2$C$\underline{H}_3$), 3.7-3.35 (m, 5H, C$\underline{H}$(CO$_2$Me)$_2$ and OC$\underline{H}_2$CH$_3$), 2.26 (dd, 2H, C$\underline{H}_2$—CH(OEt)$_2$), 1.19 (t, 6H, OCH$_2$C$\underline{H}_3$).

NMR $^{13}$C (CDCl$_3$, 50 MHz) δ (ppm): 169.7 (C, $\underline{C}$O$_2$Me), 100.7 (CH, $\underline{C}$H(OEt)$_2$), 61.9 (CH$_2$, O$\underline{C}$H$_2$CH$_3$), 52.5 (CH$_3$, CO$_2\underline{C}$H$_3$), 47.7 (CH, $\underline{C}$H(CO$_2$CH$_3$)$_2$), 32.9 ($\underline{C}$H$_2$, CH$_2$—CH(OEt)$_2$), 15.2 (CH$_3$, OCH$_2\underline{C}$H$_3$).

IR (film, cm$^{-1}$): 2977, 2879, 1737, 1437, 1373, 1342, 1275, 1241, 1194, 1158, 1127, 1063.

Example 3

Synthesis of 2,2-Bis-(2,2-diethoxy-ethyl)-malonic acid dimethyl ester

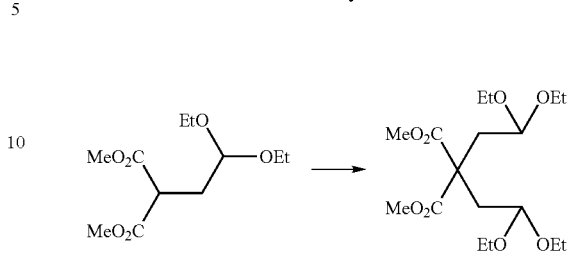

4.97 g (44.3 mmol) of $^t$BuOK are placed in a 0.5 L reactor with 80 mL DMF (solvent). 10.0 g (40.27 mmol) of 2-(2,2-diethoxy-ethyl)-malonic acid dimethyl ester, as prepared in example 2, dissolved in DMF (10 mL) are added slowly to the previous mixture keeping the temperature around 25° C. Once the addition has finished the temperature is raised to 60° C. and 7.94 mL (40.27 mmol) of bromoacetaldehyde diethyl acetal are added. The temperature is raised to 120° C. and kept during 10 h.

Then, the mixture is cooled to 50° C. and the solvent is removed in vacuo. Toluene is added to the mixture, and water is slowly added. The product is extracted into the organic layer, and then a second extraction with toluene is done. The organic layers are washed with water. The toluene is distilled off. 10.3 g (70%) of 2-(2,2-dimethoxy-ethyl)-4,4-dimethoxy-butyric acid ethyl ester are obtained as an oil.

NMR $^1$H(CDCl$_3$, 200 MHz) δ (ppm): 4.52 (t, 2H, C$\underline{H}$(OEt)$_2$), 3.70 (s, 6H, CO$_2$C$\underline{H}_3$), 3.6-3.4 (m, 8H, OC$\underline{H}_2$CH$_3$), 2.32 (d, 4H, C$\underline{H}_2$—CH(OEt)$_2$), 1.18 (t, 12H, OCH$_2$C$\underline{H}_3$).

NMR $^{13}$C (CDCl$_3$, 50 MHz) δ (ppm): 171.4 (C, $\underline{C}$O$_2$CH$_3$), 100.4 (CH, $\underline{C}$H(OEt)$_2$), 62.2 (CH$_2$, O$\underline{C}$H$_2$CH$_3$), 53.1 (C, $\underline{C}$(CO$_2$CH$_3$)$_2$), 52.3 (CH$_3$, CO$_2\underline{C}$H$_3$), 36.5 (CH$_2$, $\underline{C}$H$_2$—CH(OMe)$_2$), 15.2 (CH$_3$, OCH$_2\underline{C}$H$_3$).

IR (film, cm$^{-1}$): 2977, 2896, 1738, 1440, 1374, 1346, 1287, 1225, 1202, 1124, 1060, 1009.

Example 4

Krapcho dealcoxycarbonylation. Synthesis of 2-(2,2-Diethoxy-ethyl)-4,4-diethoxy-butyric acid methyl ester

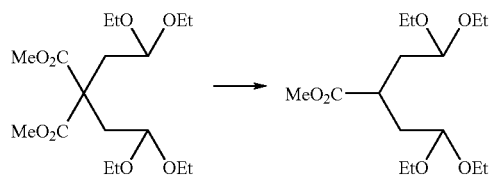

10.0 g (27.44 mmol) of 2,2-Bis-(2,2-diethoxy-ethyl)-malonic acid dimethyl ester are placed in a 0.5 L reactor with 90 mL DMF (solvent). 5.65 g (54.88 mmol) of NaBr (salt) are added. The mixture is heated to 150° C., and the temperature is kept for 12 h.

Then, the mixture is cooled to 50° C. and the solvent is removed in vacuo. Toluene is added to the mixture, and water is slowly added. The product is extracted into the organic layer, and then a second extraction with toluene is done. The organic layers are washed with water. The toluene is distilled off. 6.72 g (80%) of 2-(2,2-Diethoxy-ethyl)-4,4-diethoxy-butyric acid methyl ester are obtained as an oil (colorless).

NMR $^1$H(CDCl$_3$, 200 MHz) δ (ppm): 4.49 (t, 2H, C$\underline{H}$(OEt)$_2$), 3.62 (s, 3H, CO$_2$C$\underline{H}_3$), 3.7-3.4 (m, 8H, OC$\underline{H}_2$CH$_3$), 2.64 (m, 1H, C$\underline{H}$—CO$_2$Me), 2.1-1.9 (m, 2H, C$\underline{H}_2$CH(OEt)$_2$), 1.8-1.6 (m, 2H, C$\underline{H}_2$CH(OEt)$_2$), 1.2 (t, 12H, OCH$_2$C$\underline{H}_3$).

NMR $^{13}$C (CDCl$_3$, 50 MHz) δ (ppm): 175.9 (C, $\underline{C}$O$_2$Me), 101.3 (CH, $\underline{C}$H(OEt)$_2$), 61.7 and 61.5 (CH$_2$, O$\underline{C}$H$_2$CH$_3$), 51.5 (CH$_3$, CO$_2\underline{C}$H$_3$), 37.9 (CH, $\underline{C}$H—CO$_2$Me), 36.5 (CH$_2$, $\underline{C}$H$_2$—CH(OEt)$_2$), 15.3 (CH$_3$, OCH$_2\underline{C}$H$_3$).

IR (film, cm$^{-1}$): 2976, 2929, 2879, 1737, 1442, 1374, 1345, 1194, 1166, 1124, 1064, 1006.

In the same way, other compounds can be prepared. For example 3-[1,3]Dioxolan-2-yl-2-[1,3]dioxolan-2-ylmethyl-propionic acid methyl ester:

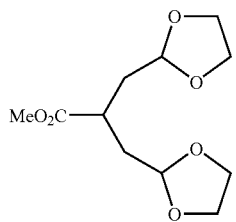

NMR $^1$H (CDCl$_3$, 200 MHz) δ (ppm): 4.93 (t, 2H), 3.98-3-78 (m, 8H), 3.65 (s, 3H), 2.81 (m, 1H), 2.20-2.04 (m, 2H), 1.93-1.77 (m, 2H).

Example 5

Synthesis of 9-methoxycarbonylmethyl-7-oxo-9-aza-bicyclo[3.3.1]no-nane-3-carboxylic acid methyl ester

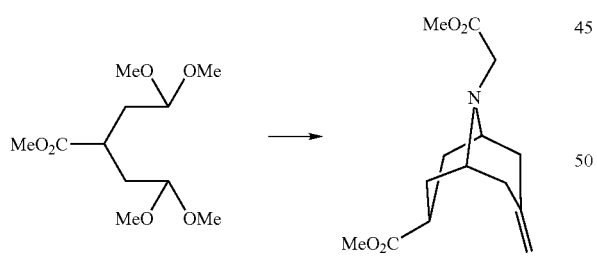

The bisacetal obtained in example 1 (100 g, 399.54 mmol) is placed in a 2 L reactor and 1 L, of 1 M aqueous solution of HCl is added. The mixture is stirred for 1 h. Then 14.4 g of citric acid are added and the pH adjusted to pH 2 with NaOH 20%.

To the solution are sequentially added 24.4 g (172.2 mmol) of Na$_2$HPO$_4$, 150.9 g (1033 mmol) of 1,3-acetonedicarboxylic acid and 173.1 g (1378 mmol) of glycine methyl ester hydrochloride. The mixture is allowed to react during 24 h at 25° C. and pH=2.

When the reaction has finished, the mixture is acidified to pH 0.8 and washed with toluene. Then the pH is raised to 6.8 using K$_2$CO$_3$ 50%, and the mixture is extracted with isopropyl acetate. The base can be isolated as it from evaporation of the solution, or transformed into the hydrochloride salt.

If desired, the hydrochloride can be prepared from an AcOiPr solution of the base by treatment with 1.05 eq. of HCl. The hydrochloride could be crystallized from IPA/5% H$_2$O. 61.1 g (50%) of 9-methoxycarbonylmethyl-7-oxo-9-aza-bicyclo[3.3.1]nonane-3-carboxylic acid methyl ester hydrochloride monohydrate, are obtained, as an off-white solid.

9-methoxycarbonylmethyl-7-oxo-9-aza-bicyclo [3.3.1]nonane-3-carboxylic acid methyl ester NMR $^1$H (CDCl$_3$, 200 MHz) δ (ppm): 3.68 (s, 3H), 3.58 (s, 3H), 3.51 (s, 2H), 3.45 (m, 2H), 2.73 (dd, 2H), 2.50 (tt, 1H), 2.25 (d, 2H), 2.01 (dt, 2H), 1.71 (dd, 2H).

NMR $^{13}$C (CDCl$_3$, 50 MHz) δ (ppm): 209.9 (C), 175.2 (C), 171.6 (C), 54.6 (CH$_2$), 54.2 (CH), 52.5 (CH$_3$), 52.4 (CH$_3$), 44.5 (CH$_2$), 33.9 (CH), 30.7 (CH$_2$).

IR (film, cm$^{-1}$): 3606, 3394, 2953, 1732, 1703, 1435, 1390, 1314, 1215, 1174, 1098, 1066, 1029.

9-methoxycarbonylmethyl-7-oxo-9-aza-bicyclo [3.3.1]nonane-3-carboxylic acid methyl ester hydrochloride monohydrate NMR $^1$H (d6-DMSO, 200 MHz) δ (ppm): 4.46 (s, 2H, C$\underline{H}_2$CO$_2$Me), 4.19 (br s, 2H C$\underline{H}$NCH$_2$CO$_2$Me), 4.6-3.2 (very br s, 1H, HCl), 3.75 (s, 3H, CO$_2$C$\underline{H}_3$), 3.61 (s, 3H, CO$_2$C$\underline{H}_3$), 3.23 (dd, 2H, (C$\underline{H}_2$)$_2$C=O), 2.55-2.04 (m, 7H, rest of the carbocycle protons).

NMR $^{13}$C (d6-DMSO, 50 MHz) δ (ppm): 204.1 (C, (CH$_2$)$_2$$\underline{C}$=O), 173.0 (C, CH—$\underline{C}$O$_2$Me), 166.8 (C, CH$_2$—$\underline{C}$O$_2$Me), 55.1 (CH, ($\underline{C}$H)$_2$—NCH$_2$CO$_2$Me), 52.7 (CH$_3$, CH—CO$_2\underline{C}$H$_3$), 52.1 (CH$_3$, CH$_2$—CO$_2\underline{C}$H$_3$), 50.7 (CH$_2$, N—$\underline{C}$H$_2$CO$_2$Me), 31.6 (CH, $\underline{C}$H—CO$_2$Me), 30.9 (CH$_2$, carbocycle).

IR (KBr tablet, cm$^{-1}$): 3460, 3409, 3000, 2956, 1746, 1721, 1630, 1433, 1416, 1384, 1136, 1326, 1317, 1236, 1199, 1176, 1062, 1036, 1024.

Water content (Karl Fisher): 5.80 (theoretical monohydrate 5.56%).

m.p. (DSC): 172-174° C. (with decomposition).

XRPD as shown in FIG. 1 (2θ): 8.5, 10.3, 11.3, 14.5, 15.1, 16.8, 19.4, 20.7, 21.0, 21.4, 21.7, 22.4, 23.8, 24.5, 25.3, 25.7, 26.0, 26.2, 26.4, 28.3, 29.5, 30.1, 30.5, 32.0, 32.5, 36.5, 37.0.

Example 6

Synthesis of endo-7-hydroxy-9-methoxycarbonylm-ethyl-9-aza-bicyclo[3.3.1]nonane-3-carboxylic acid methyl ester

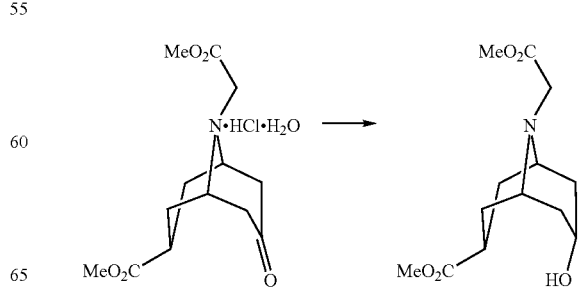

52.94 g (163.5 mmol) of the bicyclic ketone hydrochloride monohydrate obtained in example 5 are dissolved in methanol and neutralized with $Na_2CO_3$ at 0° C. 11.5 g (304.5 mmol) of $NaBH_4$ are added, and the mixture is allowed to react during 1 h. The remaining hydride is quenched with acetone, and the mixture is then neutralized with HCl. The solvent is evaporated, and the residue partitioned between AcOiPr and water. After the aqueous workup, 33.71 g (76%) of endo-7-hydroxy-9-methoxycarbonylmethyl-9-aza-bicyclo[3.3.1]nonane-3-carboxylic acid methyl ester are obtained as a colorless oil.

NMR $^1$H (CDCl$_3$, 200 MHz) δ (ppm): 4.19 (m, 1H), 3.80 (m, 1H), 3.70 (s, 3H), 3.67 (s, 3H), 3.43 (s, 2H), 3.12 (m, 2H), 2.42 (m, 2H), 2.15 (br s, 1H), 1.95 (td, 2H), 1.62-1.42 (m, 4H).

NMR $^{13}$C (CDCl$_3$, 50 MHz) δ (ppm): 176.9 (C), 171.7 (C), 61.9 (CH), 53.8 (CH$_3$), 51.7 (CH$_3$), (CH$_2$), 50.2 (CH$_2$), 35.5 (CH$_2$), 32.3 (CH), 26.9 (CH$_2$).

IR (film, cm$^{-1}$): 3444, 2927, 1732, 1436, 1300, 1248, 1203, 1115, 1033, 1002.

Example 7

Synthesis of endo-7-(1H-indole-3-carbonyloxy)-9-metho-xycarbonylmethyl-9-aza-bicyclo[3.3.1]nonane-3-carboxylic acid methyl ester

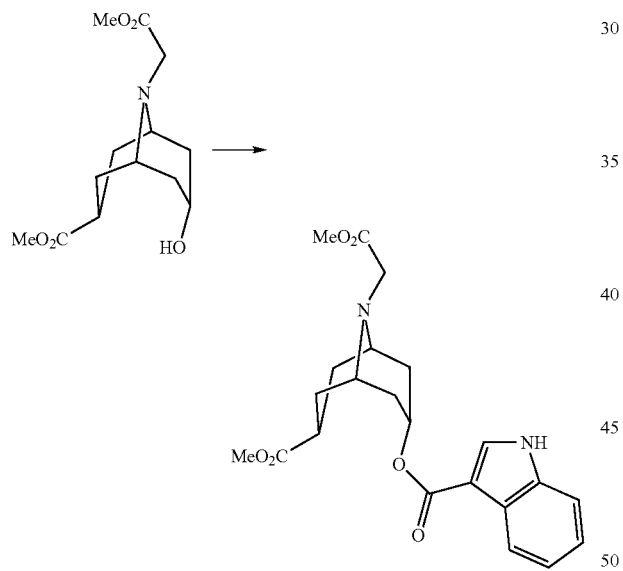

Indole-3-carboxylic acid (6.43 g, 39.9 mmol) is added in portions to a solution of 5.33 mL (37.7 mmol) of trifluoroacetic anhydride in dichloromethane (172 mL) and under nitrogen atmosphere. The resulting suspension is left under stirring for 30 minutes. endo-7-hydroxy-9-methoxycarbonylmethyl-9-aza-bicyclo[3.3.1]nonan-3-carboxylic methyl ester acid (6 g, 22.1 mmol) dissolved in dichloromethane (15 mL) is then added dropwise. Next, a catalytic amount of DMAP is added, and the suspension is then left under stirring for 4 h. Water (50 mL) is added to the reaction mixture and the mixture is basified with a saturated aqueous solution of sodium bicarbonate. Following filtration to remove the remains of indole-3-carboxylic acid in excess, the resulting phases are separated. The organic phase is dried over magnesium sulfate and evaporated to dryness to give endo-7-(1H-Indole-3-carbonyloxy)-9-methoxycarbonylmethyl-9-aza-bicyclo[3.3.1]nonane-3-carboxylic acid methyl ester as a white solid (8.20 g, 89%) that can be used directly in the following synthesis step.

If desired, the hydrochloride salt of this compound can be prepared. A solution of 10 g in isopropyl alcohol (70 mL) was heated at 40° C. At this temperature, conc. HCl was added (7 mL). Once finished the addition, the mixture was cooled down, and, if necessary, seeded. After 1 h at 0° C., the solid was filtered and washed with cold isopropyl alcohol. After drying the solid, 9.5 g were obtained.

endo-7-(1H-Indole-3-carbonyloxy)-9-methoxycarbonylmethyl-9-aza-bicyclo[3.3.1]nonane-3-carboxylic acid methyl ester NMR $^1$H (CD$_3$OD, 200 MHz) δ (ppm): 8.09-8.04 (m, 1H, Ar), 7.98 (s, 1H, Ar), 7.47-7.42 (m, 1H, Ar), 7.26-7.13 (m, 2H, Ar), 5.32 (m, 1H, CHOCO), 4.01-3.94 (s, 3H, CO$_2$CH$_3$), 3.72 (s, 3H, CO$_2$CH$_3$), 3.62 (s, 2H, CH$_2$CO$_2$Me), 3.53 (m, 1H, CHCO$_2$Me), 3.16 (m, 2H, (CH)$_2$N), 2.63-2.44 (m, 2H, carbocycle), 2.18-1.93 (m, 2H, carbocycle), 1.78-1.63 (m, 4H, carbocycle).

NMR $^{13}$C (CD$_3$OD, 50 MHz) δ (ppm): 178.3, 173.5 and 166.2 (C, CO$_2$), 138.1 (C, Ar), 133.1 (CH, Ar), 127.3 (C, Ar), 123.7 (CH, Ar), 122.5 (CH, Ar), 121.8 (CH, Ar), 112.9 (CH, Ar), 108.6 (C, Ar), 65.6 (CH, CH—OCOindol), 54.5 (CH$_2$, CH$_2$CO$_2$Me), 52.2 and 52.1 (CH$_3$, CO$_2$CH$_3$), 51.3 (CH, (CH)$_2$N), 34.0 (CH, CHCO$_2$Me), 32.5 and 29.0 (CH2, carbocycle).

IR (KBr tablet, cm–1): 3284, 2944, 1744, 1736, 1710, 1528, 1448, 1217, 1172, 1101, 1024, 751.

m.p.=152-155° C.

endo-7-(1H-indole-3-carbonyloxy)-9-methoxycarbonylmethyl-9-aza-bicyclo[3.3.1]nonane-3-carboxylic acid methyl ester hydrochloride NMR $^1$H (d6-DMSO, 200 MHz) δ (ppm): 12.37 (br s, 1H), 10.85 (br s, 1H), 8.08-7.94 (m, 2H), 7.55-7.50 (m, 1H), 7.23-7.15 (m, 2H), 5.23 (m, 1H), 4.37 (s, 2H), 4.10-3.82 (m, 3H), 3.76 (s, 3H), 3.60 (s, 3H), 2.95-1.87 (m, 8H).

IR (KBr tablet, cm$^{-1}$): 3148, 3103, 3082, 3060, 3026, 2924, 2850, 2510, 1743, 1727, 1700, 1601, 1493, 1452, 1175, 1028, 756, 702, 540.

Figure 3:
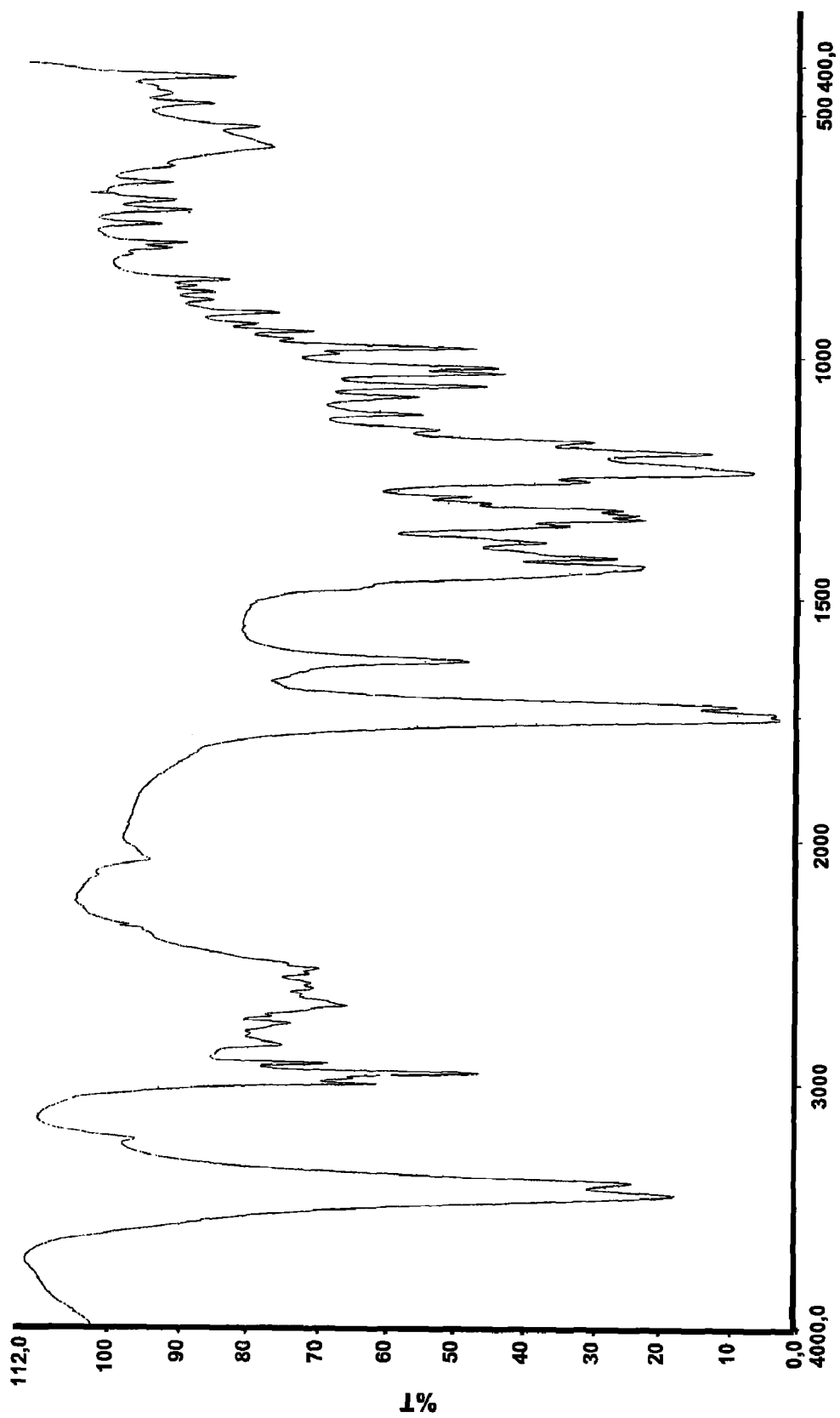
FIG. 3: XRPD of polymorph form I of 7-(1H-Indole-3-carbonyloxy)-9-methoxycarbonylmethyl-9-aza-bicyclo[3.3.1]nonane-3-carboxylic acid methyl ester hydrochloride (V·HCl).
Figure 4:
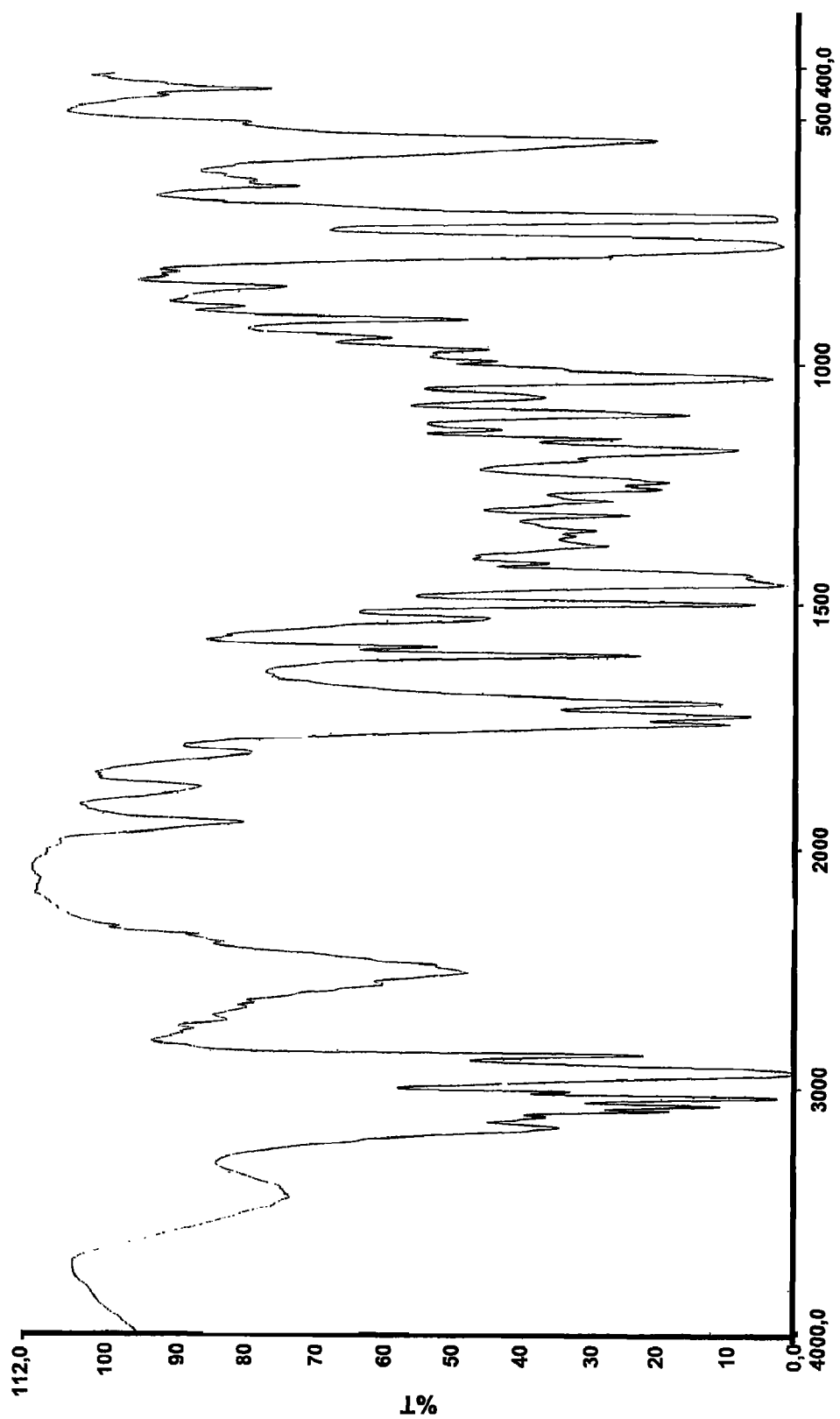
FIG. 4: IR of polymorph form I of 7-(1H-Indole-3-carbonyloxy)-9-methoxycarbonylmethyl-9-aza-bicyclo[3.3.1] nonane-3-carboxylic acid methyl ester hydrochloride (V·HCl).

XRPD (2θ) as shown in FIG. 3: 8.1, 9.2, 12.4, 13.1, 14.5, 14.7, 15.7, 16.2, 16.5, 16.8, 17.4, 18.5, 18.7, 19.0, 19.5, 20.6, 21.0, 21.9, 22.7, 23.0, 23.3, 23.5, 23.9, 25.2.

m.p. (DSC): 240-242° C. (with decomposition).

Example 8

Synthesis of endo-5-(1H-Indole-3-carbonyloxy)-10-oxo-8-aza-tricyclo[5.3.1.0$^{3,8}$]undecane-9-carboxylic acid methyl ester

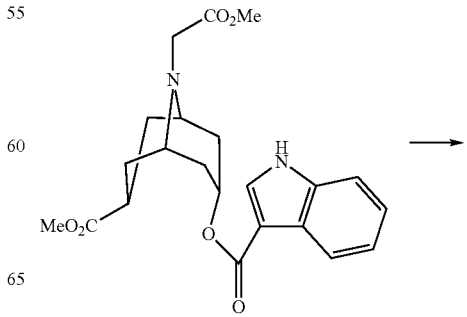

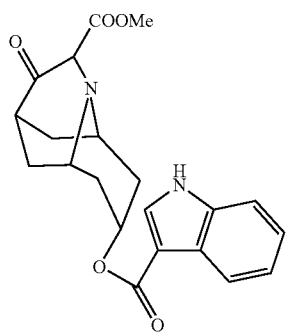

endo-7-(1H-Indole-3-carbonyloxy)-9-methoxycarbonyl-methyl-9-aza-bicyclo[3.3.1]nonane-3-carboxylic acid methyl ester (4.87 g, 11.75 mmol) dissolved in THF (150 mL) is added to a mixture of potassium tert-butoxide (5.26 g, 46.9 mmol) in THF (150 mL), under nitrogen. The resulting suspension is stirred for 3 h, until the starting product has been used up as shown by fine-layer chromatography (AcOEt/MeOH 9:1). When the reaction is considered completed, water is added and the pH adjusted to 7.5 with 1 M hydrochloric acid. The product is extracted with dichloromethane, and the organic phase is dried and evaporated, to provide 5-(1H-Indole-3-carbonyloxy)-10-oxo-8-aza-tricyclo[5.3.1.0$^{3,8}$]undecane-9-carboxylic acid methyl ester as a solid (3.63 g, 81%).

NMR $^1$H (d6-DMSO, 200 MHz) δ (ppm): 11.90 (broad s, 1H, NH), 8.08-8.00 (m, 1H, Ar), 7.98 (s, 1H, Ar), 7.53-7.43 (m, 1H, Ar), 7.25-7.10 (m, 2H, Ar), 5.31 (m, 1H, CHOCOindole), 4.26 (s, 1H, CHCO$_2$Me), 3.68 (s, 3H, CO$_2$CH$_3$), 3.68-3.55 (m, 1H, CHCOCHCO$_2$Me), 2.50-2.35 (m, 4H), 2.21-2.04 (m, 6H).

IR (KBr tablet, cm$^{-1}$): 3295, 2953, 2929, 1735, 1720, 1703, 1530, 1439, 1314, 1284, 1267, 1182, 1127, 1060, 1032, 760.

m.p.: 197-215° C.

Example 9

Synthesis of endo-hexahydro-8-(3-indolylcarbonyloxy)-2,6-methano-2H-quinolizin-3(4H)-one (Dolasetron base)

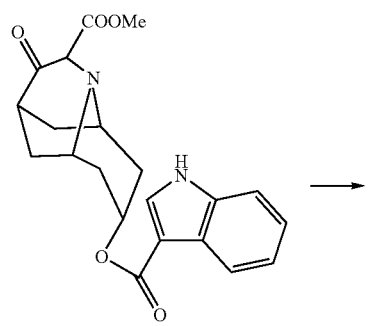

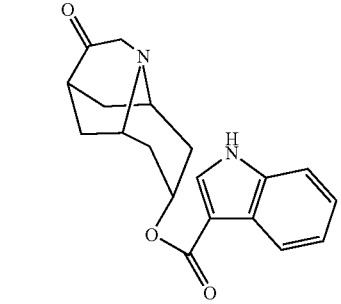

A mixture of 3.1 g (8.1 mmol) of endo-5-(1H-Indole-3-carbonyloxy)-10-oxo-8-aza-tricyclo[5.3.1.0$^{3,8}$]undecane-9-carboxylic acid methyl ester and LiCl (0.69 g, 16.23 mmol) in dimethylformamide (90 mL) is heated to 140° C. Once 4 hours have elapsed, and after checking by fine-layer chromatography (AcOEt/MeOH 9:1) that the reaction has been completed, the mixture is left to cool. Volatile substances are evaporated at low pressure and the residue is dissolved in dichloromethane (150 mL). This is washed with a saturated aqueous solution of NaCl (70 mL), and the organic phase is dried over magnesium sulfate and evaporated, to provide crude endo-hexahydro-8-(3-indolylcarbonyloxy)-2,6-methano-2H-quinolizin-3(4H)-one as a solid (2.18 g, 83%). An analytical sample was dissolved in hot AcOEt and filtered, next hexane was added, cooled and filtered.

m.p.: 230-232° C.

Figure 5:
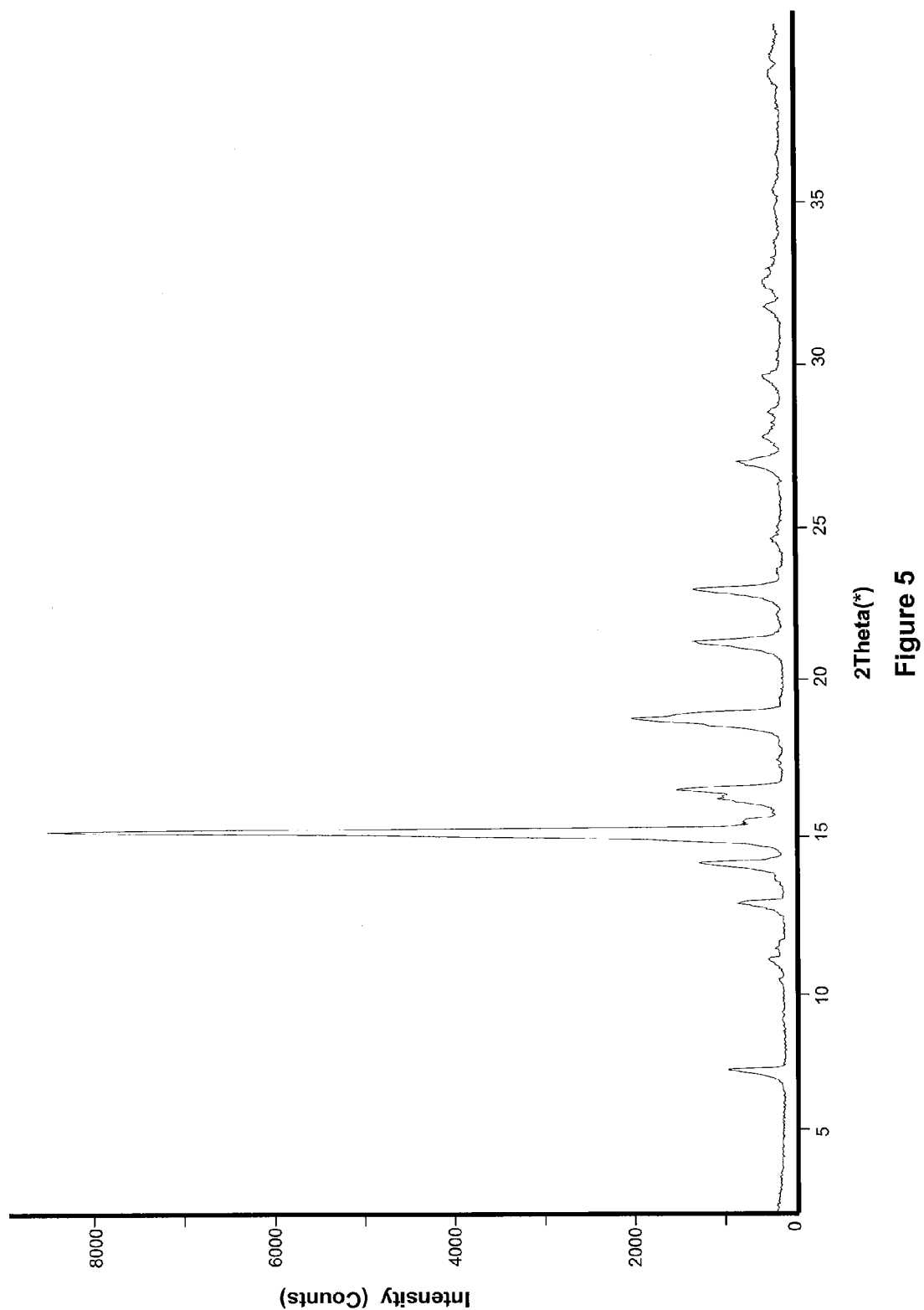
FIG. 5: XRPD of Polymorph Form I of Dolasetron base (I).

XRPD (2θ) as shown in FIG. 5: 7.6, 12.9, 14.1, 15.2, 15.5, 16.2, 16.5, 18.7, 18.9, 21.1, 22.8, 26.8.

This procedure is as described in Example 8 of EP0339669.

NMR $^1$H (d6-DMSO, 200 MHz) δ (ppm): 11.90 (broad s, 1H, NH), 8.08-8.04 (m, 1H, Ar), 7.00 (s, 1H, Ar), 7.53-7.49 (m, 1H, Ar), 7.53-7.49 (m, 2H, Ar), 5.31 (broad s, 1H, CHOC-Oindol), 3.24 (s, 2H, CH$_2$CO), 3.24-3.18 (m, 2H, (CH)$_2$NCH$_2$CO), 2.50-2.33 (m, 3H, carbocycle), 2.12-1.95 (m, 6H, carbocycle).

NMR $^{13}$C (d6-DMSO, 50 MHz) δ (ppm): 219.8 (C, C—CO—C), 163.6 (C, CO$_2$), 136.6 (C, Ar), 132.2 (CH, Ar), 126.0 (C, Ar), 122.6 (CH, Ar), 121.5 (CH, Ar), 120.3 (CH, Ar), 112.6 (CH, Ar), 106.8 (C, Ar), 65.6 (CH, CHOCO), 63.0 (CH$_2$, N—CH$_2$—CO), 47.7 (CH, (CH)$_2$—N), 40.9 (CH, CHCO), 34.5 and 29.0 (CH$_2$, carbocycle).

IR (KBr tablet, cm$^{-1}$): 3281, 2927, 1717, 1682, 1523, 1430, 1307, 1176, 1125, 1066, 1035, 766, 752, 717.

Example 10

Synthesis of endo-hexahydro-8-(3-indolylcarbonyloxy)-2,6-methano-2H-quinolizin-3(4H)-one methanesulphonate monohydrate (Dolasetron mesylate monohydrate)

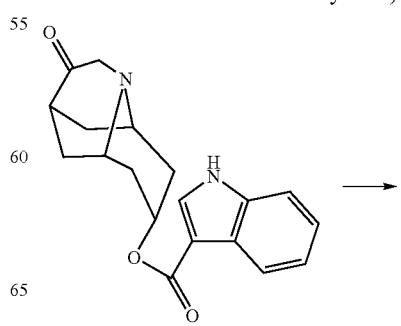

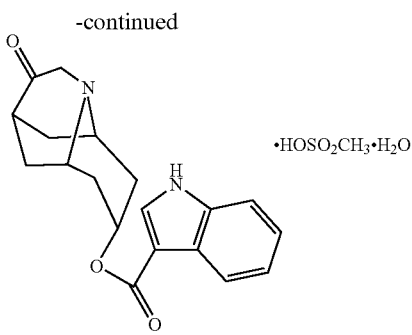

·HOSO₂CH₃·H₂O

Methanesulphonic acid (0.34 mL, 5.24 mmol) is added to a solution of endo-hexahydro-8-(3-indolylcarbonyloxy)-2,6-methano-2H-quinolizin-3(4H)-one (1.6 g, 4.93 mmol) in 20 mL acetone/water (10:3) and under nitrogen, maintaining the reaction temperature around 25° C. Following stirring at 0° C. for 3 h, and at room temperature for one night, the solid that forms is filtered and washed with acetone. The product formed is recrystallised from isopropanol-water (95:5 by weight), to obtain endo-hexahydro-8-(3-indolylcarbonyloxy)-2,6-methano-2H-quinolizin-3(4H)-one methanesulphonate monohydrate (1.71 g, 79%) as a white solid.

NMR ¹H (d6-DMSO, 200 MHz) δ (ppm): 12.00 (broad s, 1H, NH), 10.39 (broad s, 1H, MsOH), 8.08-7.97 (m, 2H, Ar), 7.60-7.47 (m, 1H, Ar), 7.31-7.14 (m, 2H, Ar), 5.38 (broad s, 1H, CHOCOindol), 4.12 (s, 2H, CH₂CO), 4.02-3.90 (m, 2H, (CH)₂NCH₂CO), 2.63-2.50 (m, 3H, carbocycle), 2.38-2.22 (m, 9H, carbocycle).

NMR ¹³C (d6-DMSO, 50 MHz) δ (ppm): 204.6 (C, C—CO—C), 163.1 (C, CO₂), 136.7 (C, Ar), 132.7 (CH, Ar), 126.1 (C, Ar), 122.8 (CH, Ar), 121.7 (CH, Ar), 120.2 (CH, Ar), 112.7 (CH, Ar), 106.0 (C, Ar), 62.9 (CH, CHOCO), 59.2 (CH2, CH₂CO), 49.9 (CH, (CH)₂NCH₂CO), 39.94 (CH, CHCO), 37.6 (CH₃SO₃), 31.9 and 25.4 (CH₂, carbocycle).

IR (KBr tablet, cm⁻¹): 3499, 3246, 2984, 2933, 2782, 2507, 1757, 1697, 1523, 1434, 1422, 1377, 1357, 1342, 1311, 1255, 1209, 1173, 1103, 1055, 1032, 779, 759.

m.p.: 160-163° C.

Water content (Karl Fisher): 4.14% (theoretical monohydrate 4.11%).

The invention claimed is:

1. A compound of formula (VII):

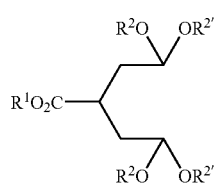

VII wherein,

R¹ is C₁-C₆ branched or linear alkyl, and

R² and R²' are independently a C₁-C₆ branched or linear alkyl.

2. The compound according to claim 1, wherein R¹, R² and R²' are independently methyl or ethyl.

3. The compound according to claim 2, wherein R¹, R² and R²' are methyl.

4. A process for preparing a compound of formula (VII) as defined in claim 1, comprising the dealkoxycarbonylation of a compound of formula (VIII) in the presence of a salt and a solvent:

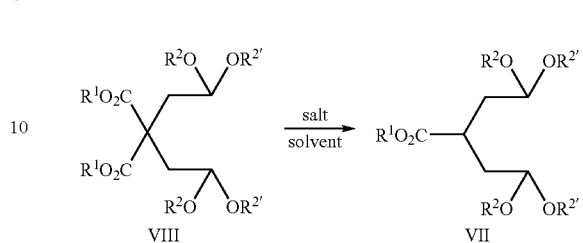

wherein R¹, R² and R²' are as previously defined.

5. The process according to claim 4, wherein the salt is selected from the group consisting of LiCl, NaCl, LiBr, NaBr, KBr and NaI.

6. The process according to claim 4, which further comprises the previous dialkylation of the malonate of formula (XI) with a compound of formula (XII) in the presence of a base and a solvent to obtain the compound of formula (VIII):

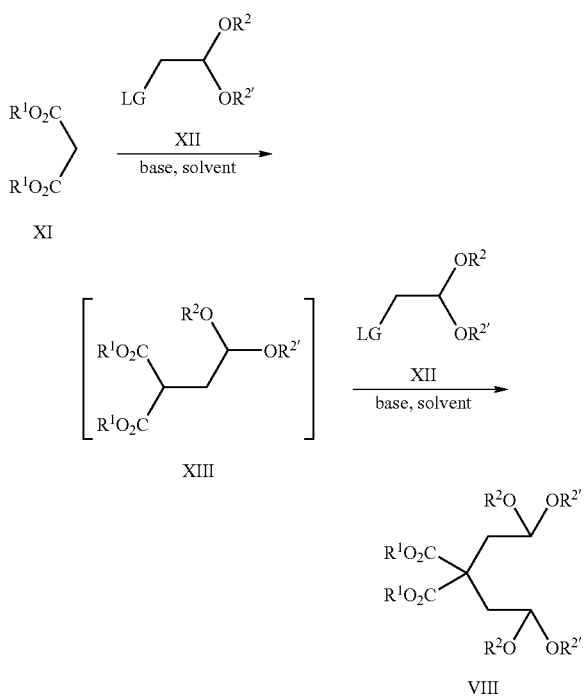

wherein R¹, R² and R²' are as previously defined and LG is a leaving group.

7. The process according to claim 6 wherein the leaving group LG is selected from the group consisting of Cl, Br, I and OSO₂R, where R is an alkyl, an aryl, a fluorinated chain or a halogen, wherein the alkyl group is optionally substituted with one or more substituents selected from the group consisting of aryl, halo, hydroxy, alkoxy, carboxy, cyano, carbonyl, acyl, alkoxycarbonyl, amino, nitro, mercapto, alkylthio, and wherein the aryl group is optionally substituted with one or more substituents selected from the group consisting of hydroxy, mercapto, halo, alkyl, phenyl, alkoxy, haloalkyl, nitro, cyano, dialkylamino, aminoalkyl, acyl, and alkoxycarbonyl.

8. The process according to claim 6, wherein the base is a metallic hydride selected from the group consisting of LiH, NaH, KH and CaH$_2$; or a metallic alcoholate selected from the group consisting of t-BuOK, EtONa, MeONa and MeOK.

9. The process according to claim 4, wherein the solvent is a polar aprotic solvent selected from the group consisting of dimethylformamide (DMF), N-methylpyrrolidone (NMP) and dimethylacetamide (DMA).

10. The process according to claim 6, wherein the dialkylation is carried out in a one-pot reaction.

11. The process according to claim 6, wherein the dialkylation is a step-wise reaction and optionally, compound (XIII) is isolated.

12. Compound of formula (VIII):

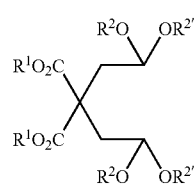

wherein
$R^1$ is $C_1$-$C_6$ branched or linear alkyl, and
$R^2$ and $R^{2'}$ are independently a $C_1$-$C_6$ branched or linear alkyl.

* * * * *

UNITED STATES PATENT AND TRADEMARK OFFICE
CERTIFICATE OF CORRECTION

| | |
|---|---|
| PATENT NO. | : 7,858,821 B2 |
| APPLICATION NO. | : 12/017709 |
| DATED | : December 28, 2010 |
| INVENTOR(S) | : Pérez Andrés et al. |

It is certified that error appears in the above-identified patent and that said Letters Patent is hereby corrected as shown below:

Title Page;

In item (12) on the cover page, please change the name of the author to:

"Pérez Andrés et al."

In column 26, please change line 65 of claim 7 to:

"nyl, acyl, alkoxycarbonyl, amino, nitro, mercapto, and alkylthio,"

Signed and Sealed this
Eighth Day of March, 2011

David J. Kappos
*Director of the United States Patent and Trademark Office*